United States Patent
Bloch et al.

(10) Patent No.: US 9,791,414 B2
(45) Date of Patent: Oct. 17, 2017

(54) METHOD AND A DEVICE FOR IDENTIFYING MATERIAL TYPES OF SPATIAL OBJECTS

(71) Applicant: SORPLA SP Z.O.O., Gdansk (PL)

(72) Inventors: Tomasz Bloch, Gdansk (PL); Grzegorz Gorczyca, Lebork (PL); Kuba Lopatka, Gdansk (PL); Iwona Gibas, Gdansk (PL)

(73) Assignee: SORPLA SP. Z O.O., Gdańsk (PL)

( * ) Notice: Subject to any disclaimer, the term of this patent is extended or adjusted under 35 U.S.C. 154(b) by 51 days.

(21) Appl. No.: 14/414,105

(22) PCT Filed: Aug. 5, 2013

(86) PCT No.: PCT/PL2013/000101
§ 371 (c)(1),
(2) Date: Jan. 10, 2015

(87) PCT Pub. No.: WO2014/025273
PCT Pub. Date: Feb. 13, 2014

(65) Prior Publication Data
US 2015/0198563 A1 Jul. 16, 2015

(30) Foreign Application Priority Data

Aug. 6, 2012 (PL) .......................................... 400249
Jul. 25, 2013 (PL) .......................................... 404841

(51) Int. Cl.
*G01D 5/12* (2006.01)
*G01N 33/44* (2006.01)
(Continued)

(52) U.S. Cl.
CPC ............... *G01N 29/04* (2013.01); *B07C 5/34* (2013.01); *G01D 5/12* (2013.01); *G01N 29/14* (2013.01);
(Continued)

(58) Field of Classification Search
CPC ...... B07C 5/34; G01N 29/14; G01N 29/4409; G01N 29/04; G01N 33/442; G01N 2291/101; G01N 2291/0235; G01D 5/12
(Continued)

(56) References Cited

U.S. PATENT DOCUMENTS 4,197,457 A * 4/1980 Cheo .................. G01N 21/8901
250/338.1
4,555,953 A * 12/1985 Dario ........................ G01L 1/16
310/338
(Continued)

FOREIGN PATENT DOCUMENTS

DE 29 46 707 5/1981
DE 42 07 728 9/1993
(Continued)

OTHER PUBLICATIONS

Durst R S et al.: "Object Classification From Analysis of Impact Acoustics", Proceedings of the 1995 IEEE/RSJ International Conference on Intelligent Robots and Systems IROS95.
(Continued)

*Primary Examiner* — J M Saint Surin
(74) *Attorney, Agent, or Firm* — Andrew Malarz

(57) ABSTRACT

The present invention relates to a method for identifying material types of spatial objects characterized in that the method comprising obtaining an acoustic signal from each identified object by deforming the objects mechanically, recording said acoustic signal and comparing it to an acoustic model being obtained on the basis of analysis of reference objects of multiple material types. The present invention also relates to a device for identifying material types of spatial objects, comprising a deformation chamber (K), a mechanical deformation system (F), at least one electro-acoustic transducer (1), an acoustic signal recording assembly (2) and a data processing unit (3) with installed acoustic
(Continued)

Figure 1:
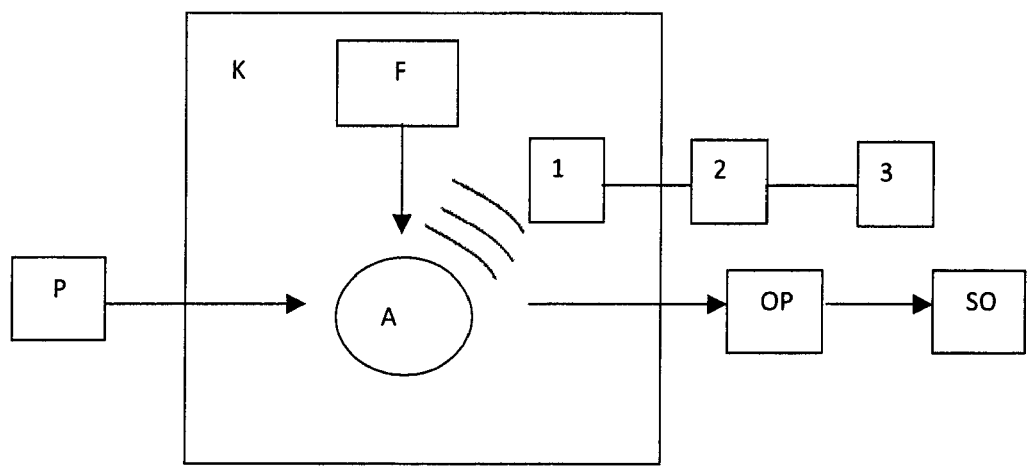

model being obtained on the basis of analysis of reference objects of multiple material types.

8 Claims, 5 Drawing Sheets

(51) Int. Cl.
    *B07C 5/34*     (2006.01)
    *G01N 29/44*     (2006.01)
    *G01N 29/14*     (2006.01)
    *G01N 29/04*     (2006.01)

(52) U.S. Cl.
    CPC ....... *G01N 29/4409* (2013.01); *G01N 33/442* (2013.01); *G01N 2291/0235* (2013.01); *G01N 2291/101* (2013.01)

(58) Field of Classification Search
    USPC .......................................................... 73/645
    See application file for complete search history.

(56) References Cited

U.S. PATENT DOCUMENTS

| | | |
|---|---|---|
| 5,501,344 A | 3/1996 | Kaiser et al. |
| 5,979,240 A | 11/1999 | Rix et al. |
| 6,026,686 A | 2/2000 | Hattori et al. |
| 6,739,194 B1 | 5/2004 | Yancey et al. |
| 2012/0217403 A1* | 8/2012 | Sartorius ............ G01N 21/3581 250/339.12 |

FOREIGN PATENT DOCUMENTS

| | | | |
|---|---|---|---|
| JP | 08150621 | | 6/1996 |
| JP | 8150621 | * | 11/1996 |
| WO | WO2009074220 | * | 6/2009 |

OTHER PUBLICATIONS

Yella et al.: "Comparison of pattern recognition techniques for the classification of impact acoustic emissions", Transportation Research, Part C.Emer. Technologies, vol. 15.

* cited by examiner

METHOD AND A DEVICE FOR IDENTIFYING MATERIAL TYPES OF SPATIAL OBJECTS

The present invention relates to a method and device for identifying material types of spatial objects, in particular plastic waste objects. The invention allows to identify a variety of material types which the objects are made of such as plastics, glass, metal, cardboard, wood, types of plastics regarding the chemical group of polymer or copolymer and additives as well as to confirm and control the quality of materials which the objects are made of. In particular, the present invention is directed to a method and a device for identifying types of material which waste products are made of and for sorting them.

The known methods for identifying type of analysed materials involve such techniques as spectroscopy, laser lights emission, hydrocyclone, electrostatics, flotation or are based on censor centrifugal separator. A number of drawbacks and limitations of the known methods are described. Spectroscopy and laser methods have high material identifying effectiveness but also large investment costs are needed, high failure rate requires very clean materials and the users of laser-based methods can be exposed to harmful radiation. A hydrocyclone method is characterised by high effectiveness but its main disadvantage is high failure rate due to high cylinder rotation speed. The significant drawback of flotation and methods that use chemical solvents is production of toxic and harmful to the environment substances. Even though electrostatic method can be also characterised by high effectiveness and does not require uniform material fragmentation, it is applicable only for dry and clean material.

It would be beneficial to provide a specific method and a device for identifying and sorting a variety of material types, which can be utilized for brand-new as well as for waste materials occurring in each household. The effectiveness of method performance should be at least competitive to the solutions described above and also properly related with price and users' needs. Favourably the method and device should be environmentally-friendly, not producing any radiation nor chemicals, not demanding high costs nor professional skills to operate. As the method and device, especially in case of waste materials, would be applied in places where such materials are stored, they should be resistant to these conditions, and preferably easy to transport and clean.

The patent application U.S. Pat. No. 5,501,344 discloses a method for identifying and sorting randomly-shaped or plane material based on irradiation of the surface structure of the identified material with electromagnetic waves in the range of UV or visible light. According to this invention, the materials are irradiated and the structures of the materials are determined by identification of the waves, which arrive from the irradiated materials. The device according to the invention comprises a receiver-sensor mean for recording the image producing waves arriving from the irradiated material which is equipped with a data logger having stored data relating to a sufficient number of surface characteristics of randomly-shaped or plane materials and means for sorting. The method requires highly-specialized, precise and expensive devices and it can be effectively exploited under laboratory condition.

The patent publication U.S. Pat. No. 5,979,240 discloses a method and apparatus for detecting objects made of recyclable materials based on interactions of the materials with the acoustic energy which results in production of resonated acoustic energy that is received and analysed. The obtained acoustic signature is compared with known signatures of objects made of recyclable materials. Device for implementing the method comprises a transmitter for producing acoustic energy, a receiver for receiving the resonated acoustic energy, a processor connected to the receiver for receiving the signal and for analyzing the resonated acoustic energy, and comparing the calculated signature to the set of known signatures of objects made of recyclable materials, means for indicating the signature substantially corresponding to known signatures. The invention requires expensive equipment and skilled and specialized services.

Only patent application JP8150621 presents an invention characterized by analysing of acoustic signals obtained during crushing objects. The result achieved by the invention is to actively reduce of the noise created during the crushing operation. The disclosed device comprises a crushing assembly, a microphone and a digital signal processing system, for generating an inverted signal, which reduces the noise created during crushing. The method can be classified as so-called active noise reduction method, which aims to reduce the noise "at the source" in order to improve working conditions and health protection of people who are in the vicinity of the device.

Publication of U.S. Pat. No. 6,026,686 A titled "Article Inspection Apparatus" teaches that it is possible to detect the material of a container, such as cans of aluminium and iron, which are identical in shape and size to each other, by generating a hitting sound by a hitting sound generating device.

Publication of Patent Application DE 29 46 707 A1 discloses a method of checking a hardness of materials and a apparatus for performing this method.

Publication of Patent Application DE 42 07 728 A1 discloses a method of checking a quality of examined objects by stimulating emission of sound waves, registering the generated sound waves in the sound detector, and then classifying the sound spectrum of the examined objects in a neural network.

Publication of DURST et al. titled "OBJECT CLASSIFICATION FROM ANALYSIS OF IMPACT ACOUSTICS", addresses the problem of autonomously classifying objects from the sounds they make when struck, and presents results from different attempts to classify various items.

Publication of YELLA et al. titled "Comparison of pattern recognition techniques for the classification of impact acoustic emissions" discloses wood-impact acoustic examination.

Publication of U.S. Pat. No. 6,739,194 B1 titled "Method of determining physical properties of wood" teaches that a small amount of a liquid or solid is projected against the end of the log with sufficient energy to induce a stress wave. The travel time of the stress wave may be measured by an accelerometer in contact with the log.

The present invention therefore provides a specific method and device for identifying material types of spatial objects. In particular, it provides a method and device for identifying materials which the objects are made of, especially to identify and sort waste materials, in particular plastic objects.

The spatial objects are understood as any kind of three dimensional objects present in everyday life or in industrial practice usually at the end of life-cycle subjected to the recycling process or ending up in the stream of dry-waste that should be sorted and exposed to further treatment. The objects could be made of various types of materials such as plastics, glass, metal, cardboard, wood and composites of those materials. The objects made of plastics means duroplasts, thermoplastics and elastomers as well as composite polymer materials including polyethylene terephthalate (PET), high-density polyethylene (HDPE), polyvinyl chloride (PVC), low-density polyethylene (LDPE), polypropylene (PP), polystyrene (PS) or could be packages or packaging objects of any other kind. The mechanical deformation used means any kind of impact on the identified objects with or without volume or shape changes including from crushing, collision with some barrier to relative objects motion, which results in obtaining an acoustic signal from the objects.

One aspect of the invention provides a method for identifying material types of spatial objects comprising obtaining an acoustic signal from each identified object by deforming the objects mechanically, recording said acoustic signal and comparing it to an acoustic model being obtained on the basis of analysis of reference objects of multiple material types. In one aspect, the analysis of reference objects of multiple material types is performed using statistical classification of acoustic signals.

In one aspect, the deforming step is carried out in such a manner that the objects are crushed.

In one aspect, the deforming step is carried out in such a manner that the objects are set in motion with a velocity of at least 5 mm/s in relation to a solid barrier, which is located in the trajectory of the moving objects.

In one embodiment of the method, the objects are set in motion by gas preferably compressed air.

In another embodiment of the method, the objects are set in motion by the gravity.

In another embodiment of the method, the objects are set in motion by the electromagnetic force.

In another embodiment of the method, the objects are set in motion by a stream of liquid.

In one aspect, the deformation step is carried out in such a manner that the objects are hit by a solid body moving at a velocity of at least 5 mm/s.

In one embodiment of the method, the solid body is set in motion by gas, preferably compressed air.

In another embodiment of the method, the solid body is set in motion by the gravity.

In another embodiment of the method, the solid body is set in motion by the electromagnetic force.

In another embodiment of the method, the solid body is set in motion by a stream of liquid.

In one aspect, the deformation step is carried out in such a manner that the objects are hit by a stream of liquid or crushed solid body particles, preferably by a stream of sand.

Another aspect of the invention provides a device for identifying material types of spatial objects, comprising a deformation chamber, a mechanical deformation system, at least one electro-acoustic transducer, an acoustic signal recording assembly and a data processing unit with installed acoustic model being obtained on the basis of analysis of reference objects of multiple material types.

In one embodiment the mechanical deformation system comprises a crusher.

In another embodiment the mechanical deformation system comprises a means for setting the objects into motion and a stiff barrier.

In another embodiment the mechanical deformation system comprises a solid body and a drive for setting the solid body in motion.

In another embodiment the mechanical deformation system comprises a nozzle supplying liquid or crushed solid body particles preferably sand particles.

In one aspect, the device further comprising an individual objects feeder, an emptying assembly for the deformation chamber, and a sorting device.

In one aspect, the device is fitted with an electro-acoustic sensor, which works in the audible acoustic signal range, frequency 20-20000 Hz.

In another aspect, the device is mounted on a portable platform or on a motor vehicle platform.

The invention enables to identify materials which the objects are made of, especially to identify and segregate waste materials as well as to confirm the quality of materials which the objects are made of.

The advantage of the method and device over all of the previous techniques is that in can specifically identify a variety of material types in easy way. The present solution does not comprise technologically advanced and costly devices. It is environmentally-friendly, does not involves chemical solutions and other toxic substances and does not emits any radiation. It can be easily transported, so the identification and sorting process can occur in any place also at the place of material production or segregation, e.g. at the landfills. It can be easily cleaned and does not require technological knowledge and specialized skills to operate. As it does not comprise expensive equipment and devices, and can be attended by two workers, it is relatively cheap. Another advantage of the invention is its high identification effectiveness at least competitive to the solutions described above. The invention is applicable to identify material types such as cardboard, metal, plastics, glass or various types of composites. Identified objects based on these materials can be both new, and waste materials.

The invention is broadly applicable in waste treatment technology to identify various material groups. It can be utilized by producers of plastic or packaging materials, or in companies and institutions which deal in waste management.

It is an advantage of the present invention that the embodiments provide an identifying and sorting system broadly applicable in sorting plants which specialize in identification, sorting and further processing of plastics, to separate the main types of plastic materials and the most popular copolymers. The invention finds particular application in the identification and segregation of waste from selective waste collection before undergoing further recycling process by provision of identification of selective material types e.g. only the chosen waste products, such as returnable PET bottles. It is an idea of the embodiment of the present invention that the device is mounted on a portable platform or on a motor vehicle platform. The invention is also possibly fitted with additional systems known from industrial practice which make it possible to recognise the shape and material colour as well. Using a portable segregating system according to the invention enables its user to quickly place the device where the objects need to be identified, for instance in a storage yard, at the producers' or at the waste receivers'.

The additional advantage of the present method and device is to enable to thoroughly differentiate between various types of plastics, including duroplasts, thermoplastics and elastomers as well as composite polymer materials including polyethylene terephthalate (PET), high-density polyethylene (HDPE), polyvinyl chloride (PVC), low-density polyethylene (LDPE), polypropylene (PP), polystyrene (PS) and packages or packaging objects described by Society of the Plastics Industry Inc. Material Labelling System.

The device has a capacity for other industrial applications, for instance to segregate processing waste and post-industrial waste products, e.g. acrylonitrile butadiene styrene (ABS) mixed with styrene, or polyvinyl chloride (PVC) mixed with other plastics.

Figure 2:
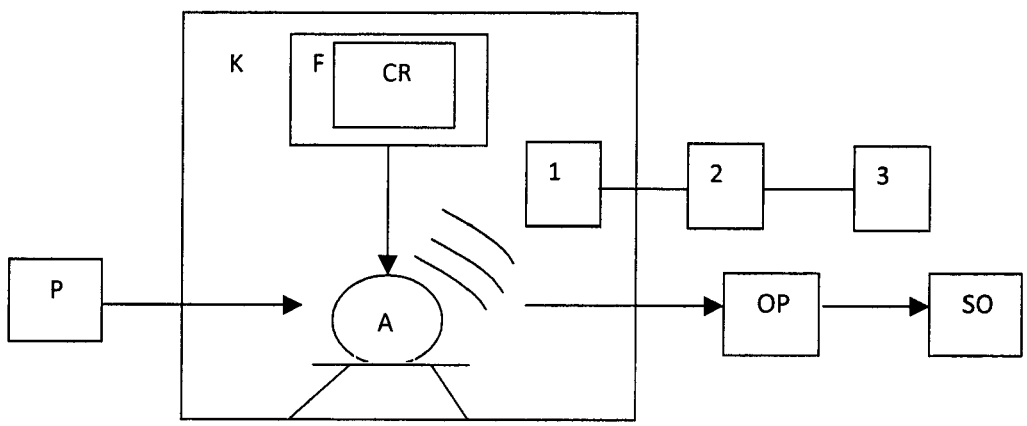
Figure 3:
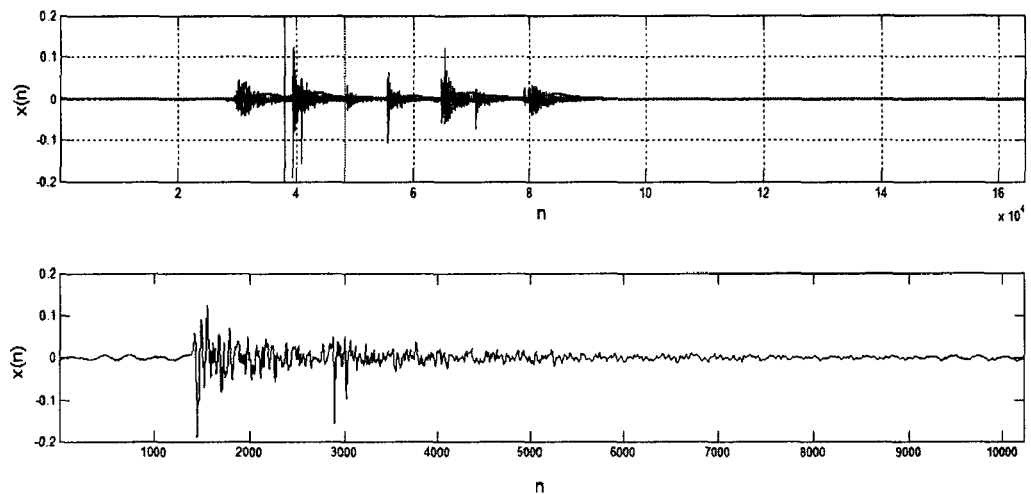
Figure 4:
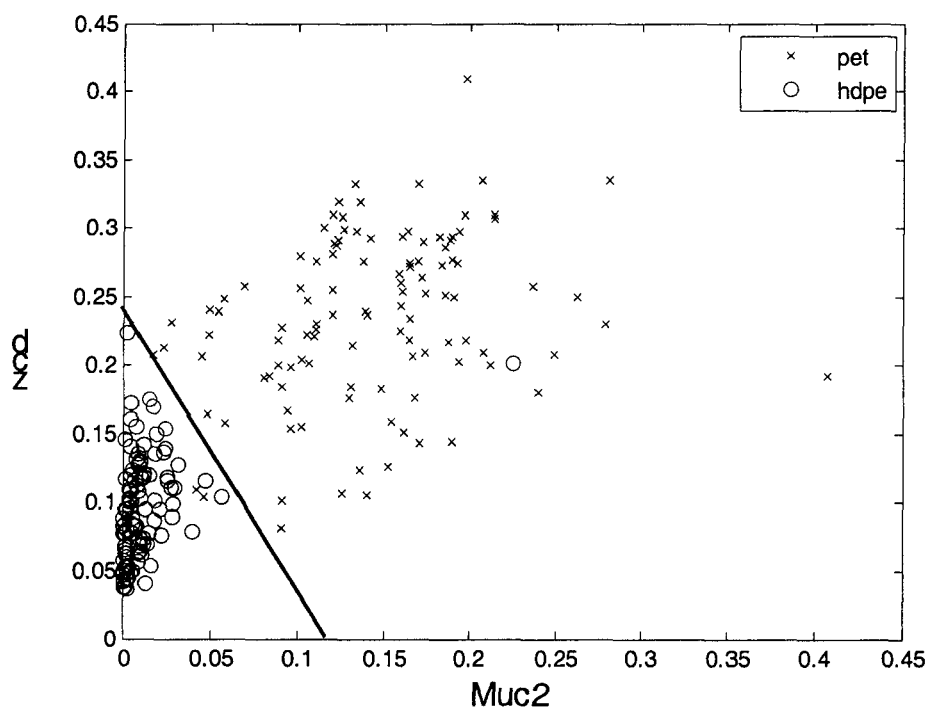
Figure 5:
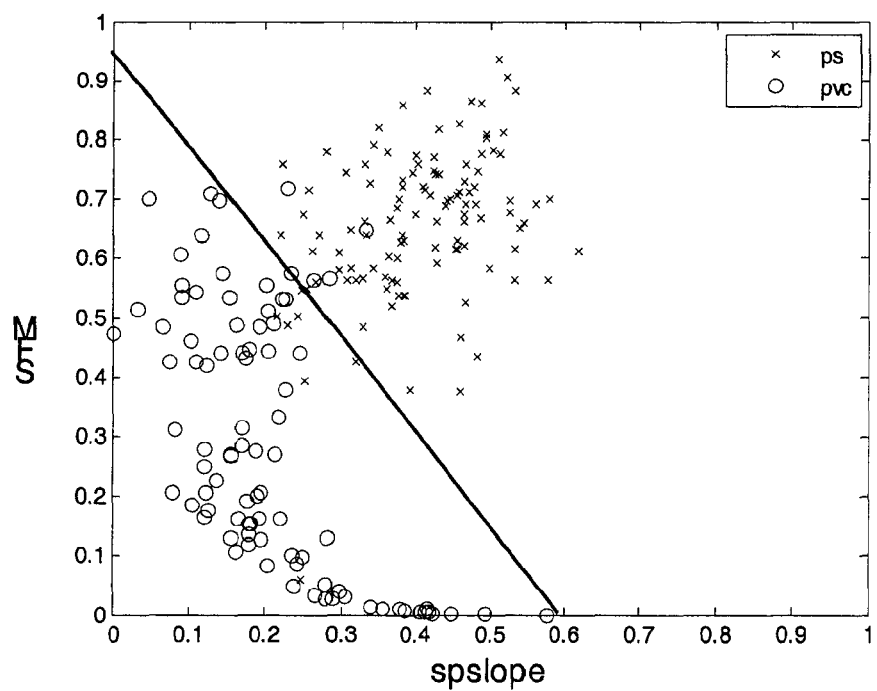
Figure 6:
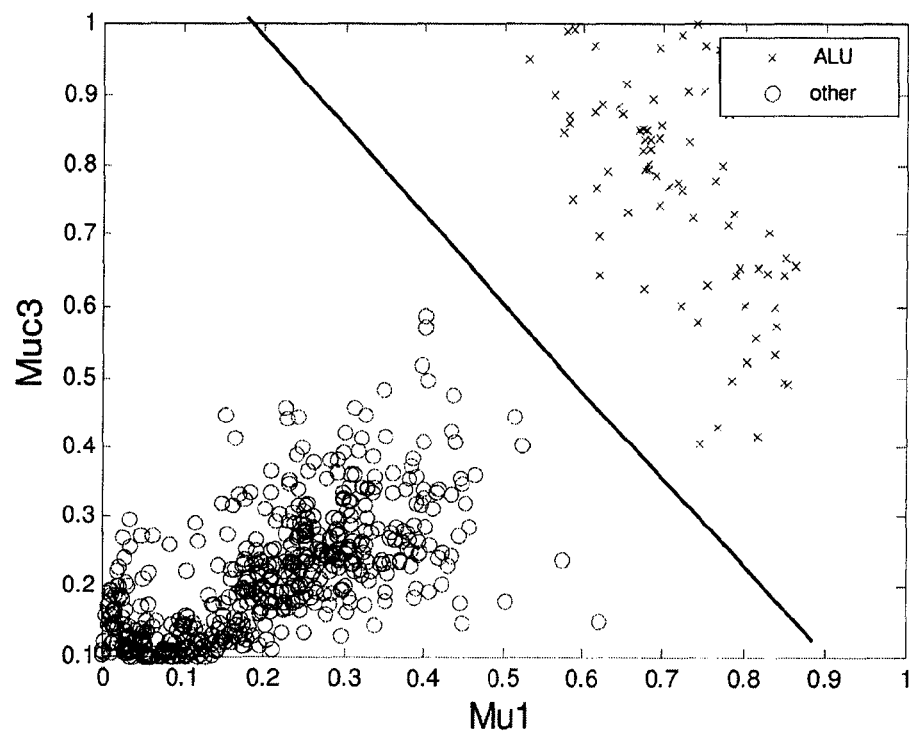
Figure 7:
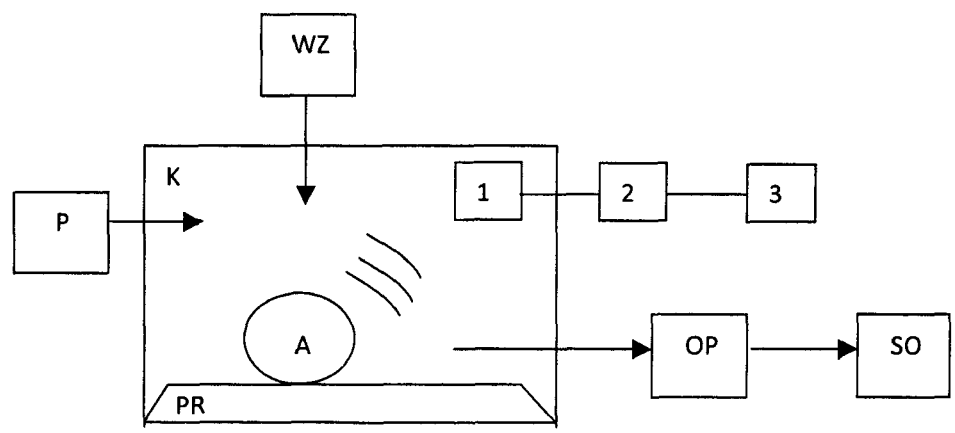
Figure 8:
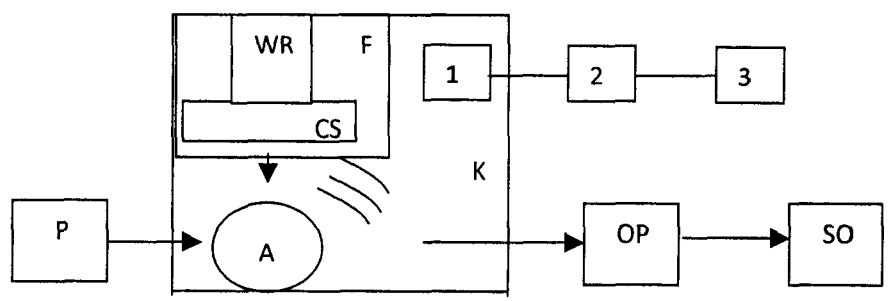
Figure 9:
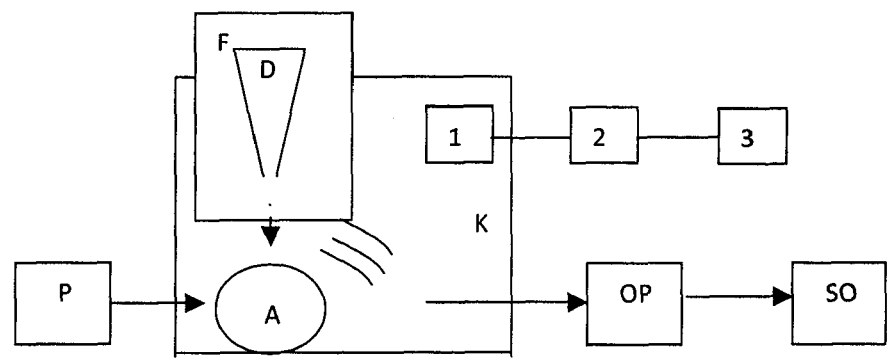
Figure 10:
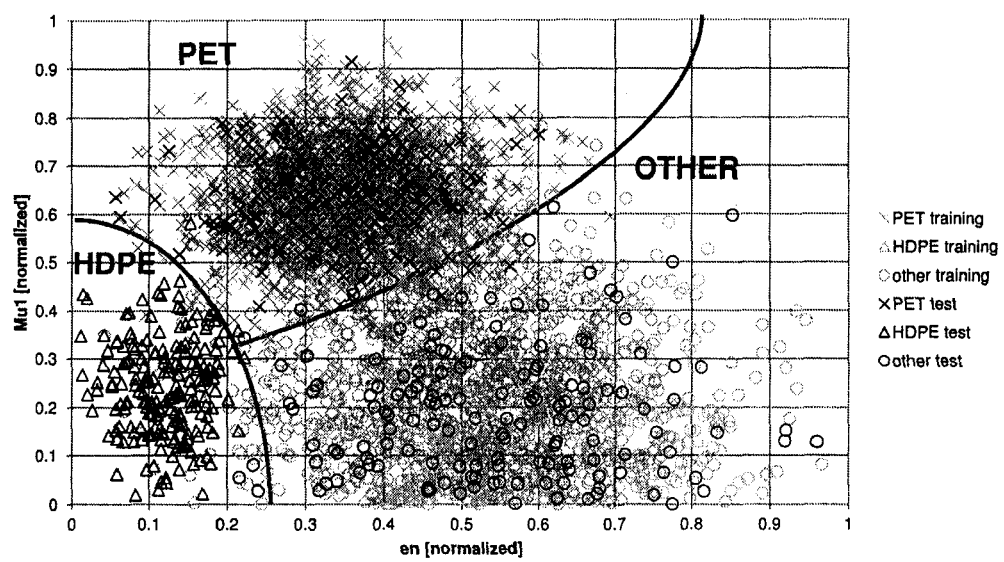

Exemplary embodiments of the present invention are illustrated in the following examples and in the accompanying drawings, in which FIG. 1 is a schematic view of the device for identifying material types of objects according to one embodiment of the disclosure, FIG. 2 is a schematic view of the device for identifying material types of objects according to the embodiment in which objects are crushed, FIG. 3 presents the example of the analysed acoustic signal with the whole registered signal shown in the upper part, and the chosen fragment of the signal shown below it, FIG. 4 presents a graphical illustration of the identification results for PET and HDPE plastics materials with the comparison to the acoustic model obtained on the basis of analysis of reference objects, FIG. 5 presents a graphical illustration of the identification results for polystyrene and PVC plastics with the comparison to the acoustic model obtained on the basis of analysis of reference objects, FIG. 6 presents a graphical illustration of identification results for aluminium cans as well as plastic packages and packaging waste with the comparison to the acoustic model obtained on the basis of analysis of reference objects, FIG. 7 is a schematic view of the device for identifying material types of objects according to the embodiment in which objects are collided with a stiff barrier, FIG. 8 is a schematic view of the device for identifying material types of objects according to the embodiment in which objects are driven into motion with the use of an actuator, FIG. 9 is a schematic view of the device for identifying material types of objects according to the embodiment in which objects are hit with a stream of crushed solid body, FIG. 10 presents the graphical illustration of the identification results for three sample groups of objects analysed by the device according to the embodiment in the FIG. 7 with the comparison to the acoustic model, The embodiments are discussed in the following examples provided to further illustrate the presented invention. The examples are not meant to limit in any manner the scope of the invention.

EXAMPLE 1

Identification of Packages and Packaging Waste from PET and HDPE a) Construction of the Device In an embodiment of the invention the device consists of a deformation chamber K, mechanical deformation system F, one electro-acoustic transducer 1 in a form of a microphone placed in the deformation chamber K, which is connected to the assembly 2 which registers acoustic signal, to which the data processing unit is connected, in a form of a computer 3 on which the acoustic signal model obtained from the analysis of model objects of multiple material types is installed. In this embodiment, shown in FIG. 2, the mechanical deformation system consists of a crusher CR. In this embodiment the crusher consists of an actuator with a solid plane pressing the object to the sides of the chamber K. The device is fitted with a feeder P, which feeds objects one by one, deformation chamber K emptying assembly OP, and a sorting device SO.

b) Creating Acoustic Signal Model Based on the Analysis of Model Objects

An acoustic signal model was obtained in the following way: a thousand of each kind of objects made of HDPE and PET are gathered and constitute a training set. Objects from the training set are fed to the machine which operates in the previously described manner. The feeder P, which feeds objects one by one, feeds the objects to the deformation chamber K, where they are mechanically deformed, in this case crushed in a specified time period. The acoustic signal created during crushing is recorded using a microphone 1 and a signal recording assembly 2, and next, the computer 3 calculates a set of acoustic signal parameters both temporal and spectral which are known from the signal processing domain. In this case two parameters characteristic for HDPE and PET were chosen: zero crossing density in the time domain zed, and second order normalised spectral moment, interpreted as a square of signal bandwidth Muc2. FIG. 3 presents the fragment of the recorded acoustic signal, with a marked fragment which was chosen for the analysis of the model object. After calculating the signal features for all objects from the model set, classifier training takes place, that is, adjusting the statistical algorithm to the model set to create the analysis model for the model objects. After recording the classification model in the device memory, it is possible to identify objects of unknown type.

c) Testing the Analysis Model for Model Objects

In order to test the analysis model for model objects, a mixed set of objects containing 111 HDPE objects and 120 objects from PET were subjected to the analysis. Objects from the testing set were fed to the machine which was operating according to the method for creating a classification model described previously. Next, after zed and Muc2 parameters were calculated for the objects from the test set, the classification algorithm assigned them to one of two types of identified objects.

The diagram from FIG. 4 presents the results of the test group object analysis described above. The sets corresponding to the PET and HDPE plastics are linearly separable and they can be differentiated on the basis of the model established from the model object set, represented as a line.

According to the model, on the graph from FIG. 4, all the points located under the line are from the set of HDPE objects, and points located over the line—from PET.

d) Identification and Segregation of Packages and Packaging Waste

Packages or packaging waste are fed individually, through the feeder P which feeds objects one by one, to the mechanical deformation chamber K. In this embodiment of the invention the deformation step is carried by crushing the objects accomplished by a crusher CR. Crushing takes place under physical conditions specified in the model, i.e. the exact same force and time of crushing is maintained. The acoustic signal created during crushing is recorded by the microphone 1 and the signal recording assembly 2. Next, the computer 3 calculates the characteristic parameters: zero crossing density in the time domain zed and second order normalised spectral moment, interpreted as a square of signal bandwidth Muc2. The computer 3 compares these parameters with the model and sends the information about the material type to the sorting device SO. The object is removed from the deformation chamber K by the chamber emptying assembly OP, and is directed to the sorting device SO, which performs the sorting process based on the information received from the computer 3.

EXAMPLE 2

Identification of Polystyrene (PS) and Polyvinyl Chloride (PVC) Objects

In the embodiment of the invention, the device is consisted as described in example I, except that it is fitted with a dampened deformation chamber K, and the model is developed as described in the example 1, except that the acoustic signal model of PS and PVC objects is created, 1000 pieces each, and the chosen and calculated parameters regarding the acoustic signals created during the object crushing process, which are known to a person skilled in the signal processing domain, are different. In order to create the model, two parameters characteristic to PS and PVC were chosen: spectral flatness measure SFM and spectral slope (spslope). The model was tested on 115 objects made of polystyrene PS and 90 polyvinyl chloride PVC objects. The diagram from FIG. 5 presents the results of model testing. According to the model, in the graph from FIG. 5, all the points located under the line are from the set of PVC objects, and points located over the line—of PS. Identification of the tested objects takes place similarly to the example 1.

EXAMPLE 3

Identification of Aluminium Objects in the Stream of Mixed Cans and Packages as Well as Plastic Packaging Waste In the embodiment of the invention the device is constructed as described in the example 1 while the acoustic signal model is developed in similar way to that described in example 1, except that the set of model objects consists of 1000 objects of aluminium cans and 1000 objects made of plastics (PET, HDPE, LDPE, PP, PS and PVC), and a different set of parameters was chosen from the acoustic signal parameters calculated for acoustic signals created during crushing objects, known to a person skilled in the signal processing domain. In order to develop the model, two parameters characteristic for the tested object groups were chosen from the set of calculated parameters: third order normalised central spectral moment—signal spectral skewness Muc3 and first order normalised spectral moment—power spectrum centroid Mu1. The model was tested on 100 aluminium can objects and 650 plastic package objects. The diagram from FIG. 5 presents the results of model testing. According to the model, on the graph from FIG. 5 all the points located under the line are from the set of plastic objects, and points located over the line from the set of aluminium cans. The identification of the tested objects takes place similarly to the example 1.

EXAMPLE 4

Identification of Material Tape of Spatially Formed Waste Objects by Putting in Motion by Direct Impact of Compressed Air a) Construction of the Device In the embodiment of the FIG. 7 device for identifying of material type of spatially formed objects, especially plastic waste objects, comprises the deformation chamber K, the mechanical deformation system F, the object feeder P, the emptying system OP, sorting device SO, electro-acoustic transducer in the form of a microphone 1, circuitry for registering the acoustic signal 2 and a data processing unit in the form of a computer 3 with an installed model acquired from analyzing exemplary objects. In the embodiment of the invention the mechanical deformation system F comprises a stiff barrier PR, and the drive WZ for setting the objects in movement with the use of directly applied compressed air.

b) Establishing a Model from Exemplary Objects

The model of analysis of exemplary objects was acquired in the following way: 2000 objects of type HDPE and PET and 2000 objects of different types, in particular 500 objects of each of the following types: ALU, PS, PP, Tetra-pack, are collected, constituting the training set. The objects from the training set are fed into the mentioned device. The system for object feeding P feeds the objects into the system for putting objects in motion WZ, which accelerates them to a velocity not smaller than 0.5 m/s by applying compressed air. Next, the objects collide with a stiff barrier PR inside the deformation chamber K. The signal emitted as a result of the collision is registered with the microphone 1 and the circuitry for registering signals 2. Subsequently, employing a computer 3 the set of signal features is calculated. The set of signal features includes temporal and spectral features known to the person trained in the technical domain, two of which are particularly distinctive for PET and HDPE types: signal energy en and 1-st order normalized spectral moment Mu1 understood as the spectral centroid of the signal. After calculating the features from all objects from the training set, the training of the classifier is performed, i.e. fitting of a statistical algorithm to the set of known patterns, which allows for establishing an acoustic model of exemplary objects. The model is written in the computer's memory.

c) Testing the Acoustic Model of Exemplary Objects.

In the process of model validation a test set, comprising 200 objects of type HDPE, 200 objects of type PET and 200 objects of other types, including 50 objects of each of the types: ALU, PP, PS, Tetra-pack, is analyzed. The objects are fed into the device described in section a). Next, after calculating the features en and Mu1 for objects from the test set, the classification algorithm assigns them to one of the two types of recognized objects.

The distribution of signal features for different material types in the multidimensional feature space allows for recognizing the type of material. It is illustrated in FIG. 10 where the distributions of parameters en and Mu1 of the signals emitted by colliding the objects with a stiff barrier are depicted.

d) Identification and Segregation of Packaging Waste Objects.

The packaging waste objects A are fed into the deformation chamber K with the feeder P and the drive for putting objects in motion WZ, accelerated to a velocity not smaller than 0.5 m/s and not greater than 10 m/s, and collided with a stiff barrier PR. The signal emitted as a result of the collision is registered by a microphone 1 and circuitry for signal registration 2. Next, the signals are analyzed with a computer 3, in which the signal features are calculated, including signal energy en and 1-st order normalized spectral moment Mu1 understood as the spectral centroid of the signal. The classification algorithm installed in the computer 3 compares the features to the acoustic model of exemplary objects, assigns them to one of the known types and sends a signal to the sorting device SO. The object A is removed from the chamber K by an emptying system UP. Subsequently, it is dropped into the sorting device SO, which sorts the object accordingly to the signal received from the computer 3.

EXAMPLE 5

Identification of Material Type of Spatially Formed Waste Objects by Putting in Motion by Gravity The recognition process is carried out by the device described in example 4, in which the objects A are put into motion by dropping from 1 meter height.

The model described in the example 4 is employed accordingly.

EXAMPLE 6

Identification of Material Type of Spatially Formed Waste Objects Based on Deformation Carried Out by Colliding Objects with a Moveable Solid Body Mounted on a Piston of a Pneumatic Actuator a) The Recognizing Device In the embodiment of FIG. 8, the device for identification of material type of spatially formed objects, especially plastic waste objects, comprises the deformation chamber K, object feeder P, the mechanical deformation system, the emptying system OP, sorting device SO, electro-acoustic transducer in the form of a microphone 1, circuitry for registering the acoustic signal 2 and a data processing unit in the form of a computer 3 with an installed model acquired from analyzing exemplary objects. In this example and embodiment the mechanical deformation system consists of an actuator WR, whose piston has a solid body CS attached to it.

b) Acquiring the Model of Exemplary Objects

The model is acquired accordingly to the example 4, the deformation step is carried in such a way that the objects are hit with a solid body moving at a velocity of at least 0.5 m/s and not greater than 10 m/s.

c) Validation of the Model of Exemplary Objects

The validation is carried out according to example 4 c), given the device described in FIG. 8 is employed.

d) Recognition and Segregation of Packaging Waste Objects

The recognition and segregation is performed according to the example 4, given the object A is hit with a solid body CS driven into motion by means in the form of an actuator whose piston moves at a velocity of at least 0.5 m/s. Subsequently, the acoustic signal emitted during the collision is registered. The signal is then analyzed according to the example 4.

EXAMPLE 7

Identification of Material Type of Spatially Formed Waste Objects by Hitting them with a Stream of Sand a) Recognizing Device In the embodiment shown FIG. 9, the device for identifying material type of spatially formed objects, especially plastic waste objects, comprises the deformation chamber K, object feeder P, the mechanical deformation system F, the emptying system OP, sorting device SO, electro-acoustic transducer in the form of a microphone 1, circuitry for registering the acoustic signal 2 and a data processing unit in the form of a computer 3 with an installed model acquired from analyzing exemplary objects. In this example, the mechanical deformation system F consists of a nozzle supplying a stream of sand D.

b) Acquiring the Model of Exemplary Objects

The model is acquired accordingly to example 4, given the objects are hit with a stream of sand flowing at a velocity of at least 0.5 m/s and not greater than 10 m/s.

c) Validation of the Model of Exemplary Objects

The validation is carried out according to example 4 c), given the device described in FIG. 9 is employed.

d) Recognition and Segregation of Packaging Waste Objects

The identification and segregation is performed according to example 1, given the object A is hit with a stream of sand flowing at a velocity of at least 0.5 m/s and not greater than 10 m/s. Subsequently, the acoustic signal emitted during the collision is registered. The signal is then analyzed according to the example 4.

The invention has been described in detail with particular embodiments, but it will be understood that variations and modifications can be effected within the spirit and scope of the invention.

The invention claimed is:

1. A method for identifying material types of spatial objects, in particular plastic objects, the method comprising
    obtaining an acoustic signal from each identified object by deforming the objects mechanically,
    recording said acoustic signal and comparing it to an acoustic model being obtained on the basis of analysis of reference objects of multiple material types, wherein the method is enabling to thoroughly differentiate between various types of plastics preferably using statistical classification of acoustic signals, wherein the objects are set in motion,
    wherein the deforming step is carried out in such a manner that the objects are crushed, and
    wherein the deforming step is carried out in such a manner that the objects are set in motion with a velocity of at least 5 mm/s in relation to a solid barrier (PR), which is located in the trajectory of the moving objects.

2. The method of claim 1, wherein the objects are set in motion by gas for best results by compressed air.

3. The method of claim 1, wherein the objects are set in motion by gravity.

4. The method of claim 1, wherein the objects are set in motion by a stream of liquid.

5. The method of claim 1, wherein the deformation step is carried out in such a manner that the objects are hit by a solid body moving at a velocity of at least 5 mm/s.

6. The method of claim 5, wherein the body is set in motion by gas, for best results by compressed air.

7. The method of claim 5, wherein the body is set in motion by gravity.

8. The method of claim 5, wherein the body is set in motion by a stream of liquid.

* * * * *